United States Patent [19]

Klein

[11] 4,445,853
[45] May 1, 1984

[54] POSITIVE RELEASE FACE-BOW/MOUTH-BOW MECHANISM

[76] Inventor: Paul E. Klein, 928 Lake Shore Rd., Lake Oswego, Oreg. 97034

[21] Appl. No.: 497,755

[22] Filed: May 25, 1983

[51] Int. Cl.³ .............................................. A61C 7/00
[52] U.S. Cl. ...................................................... 433/5
[58] Field of Search ........................................... 433/5

[56] References Cited

U.S. PATENT DOCUMENTS

| | | | |
|---|---|---|---|
| 664,412 | 12/1900 | Knapp | 433/5 |
| 3,866,322 | 2/1975 | Broussard et al. | 433/5 |
| 3,997,971 | 12/1976 | Moss | 433/5 |
| 4,212,637 | 7/1980 | Dougherty et al. | 433/5 |

*Primary Examiner*—Robert Peshock
*Attorney, Agent, or Firm*—Kolisch, Hartwell, Dickinson & Anderson

[57] ABSTRACT

A positive-separation, orthodontic, face-bow/mouth-bow mechanism, wherein a spring device effects sure separation of a disengageable face-bow and mouth-bow under circumstances when, during normal usage, compression transmission through these devices relaxes.

18 Claims, 9 Drawing Figures

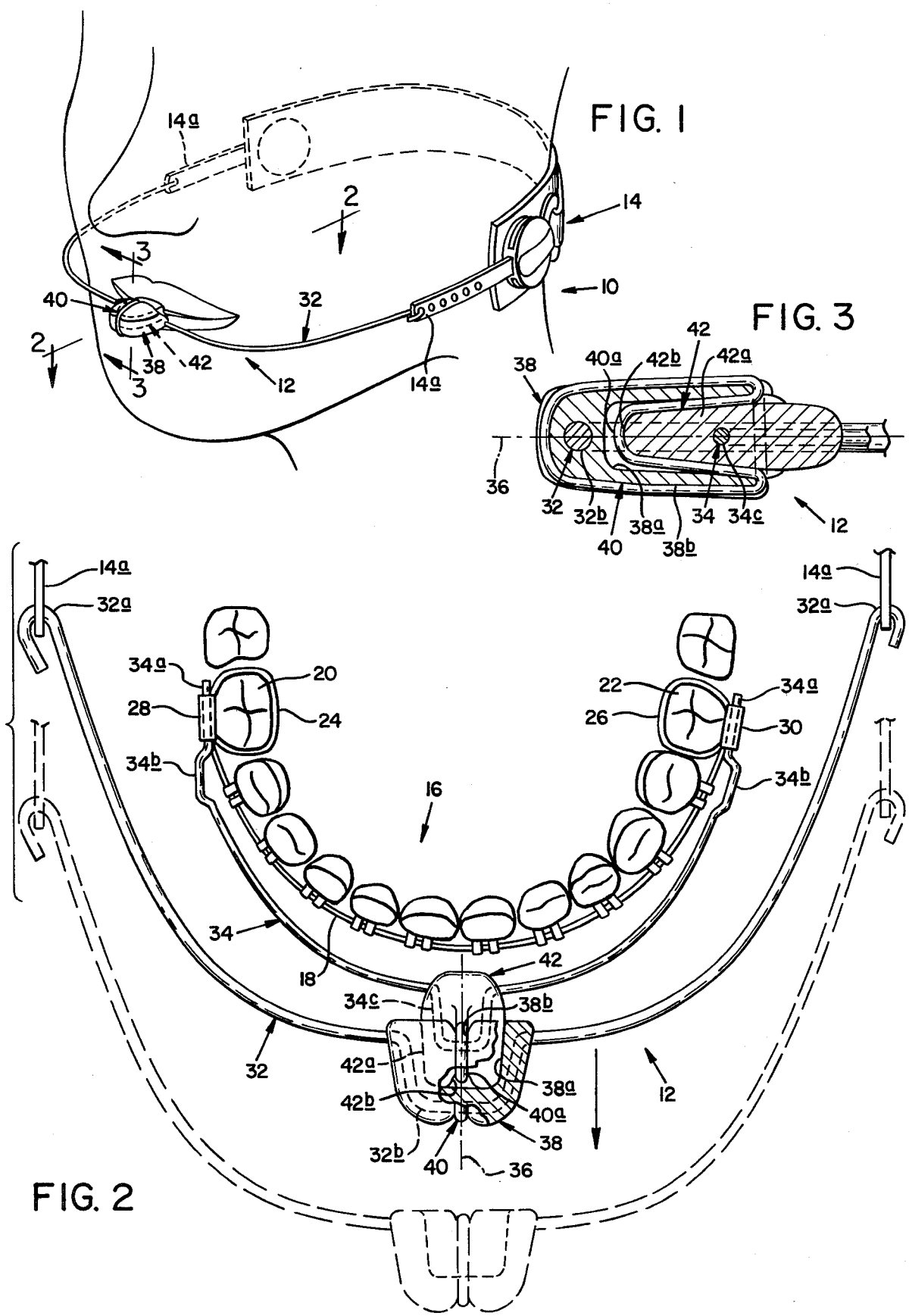

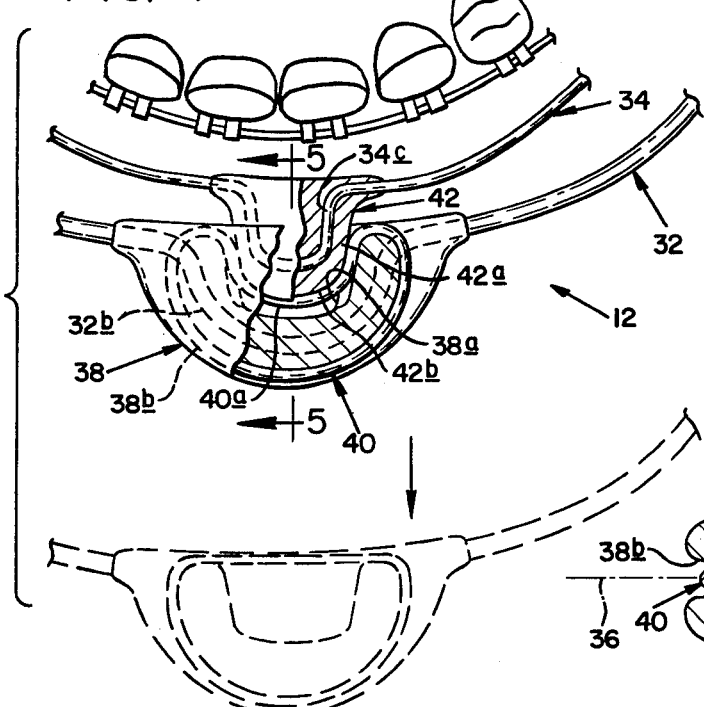
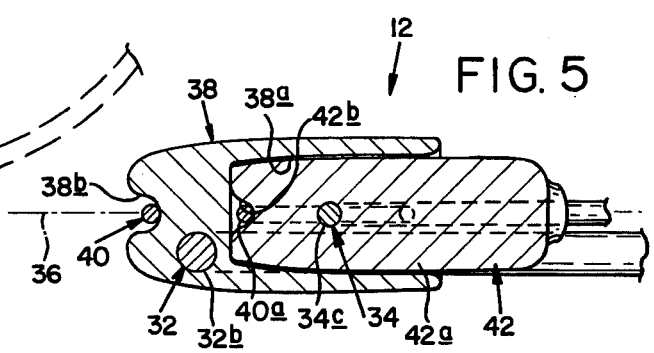
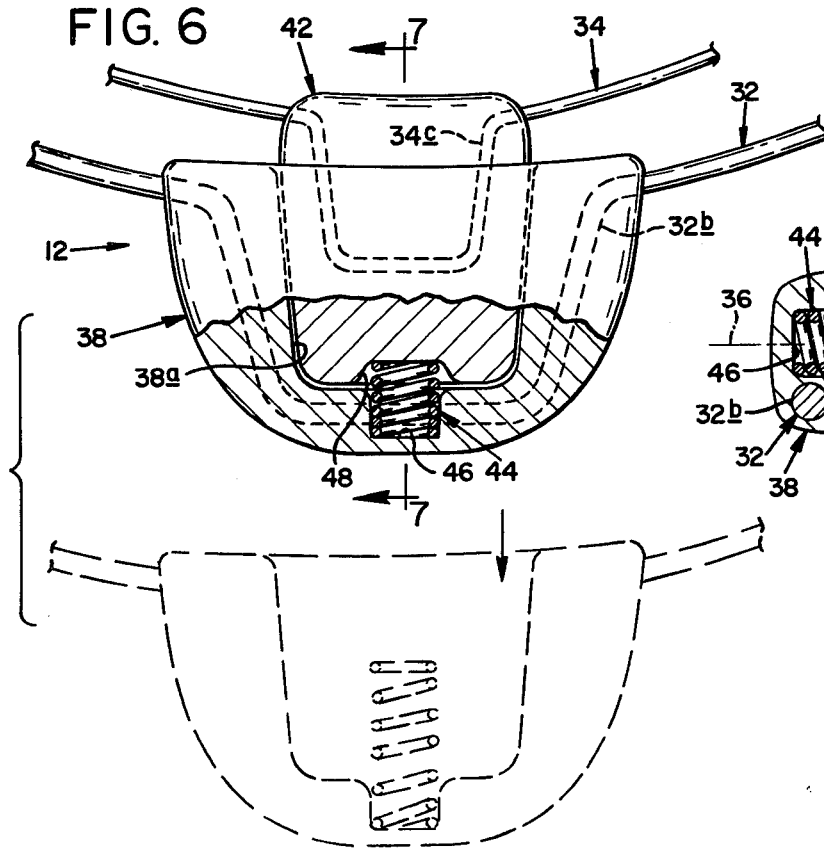

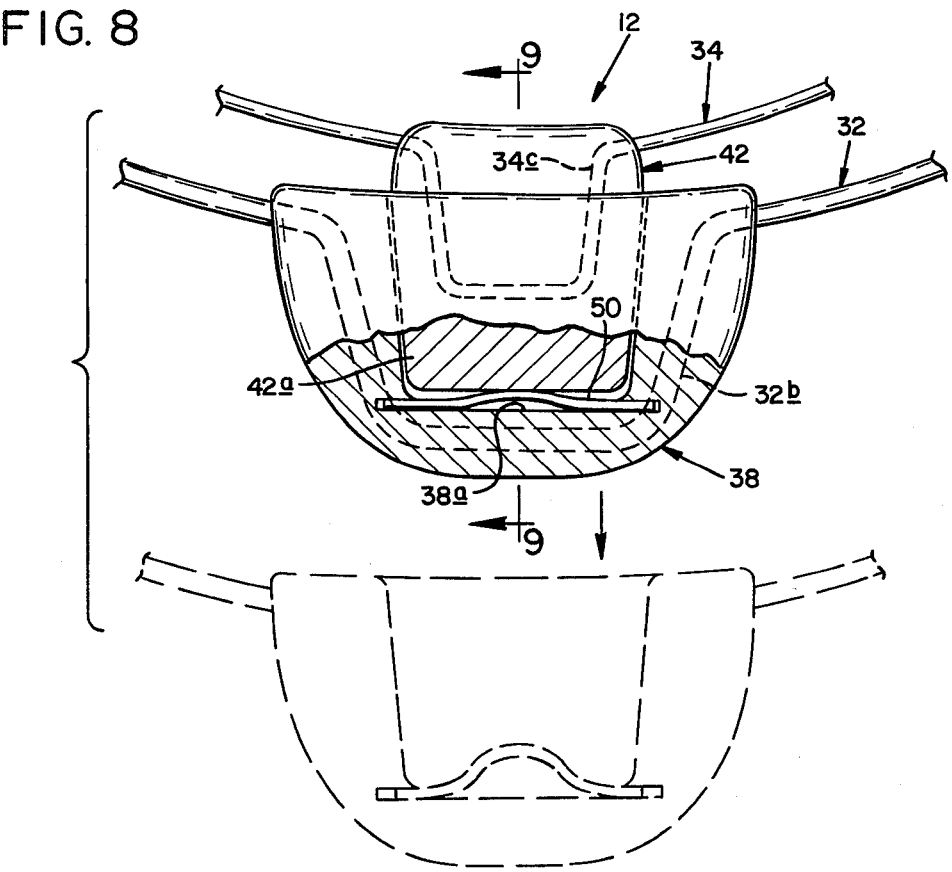
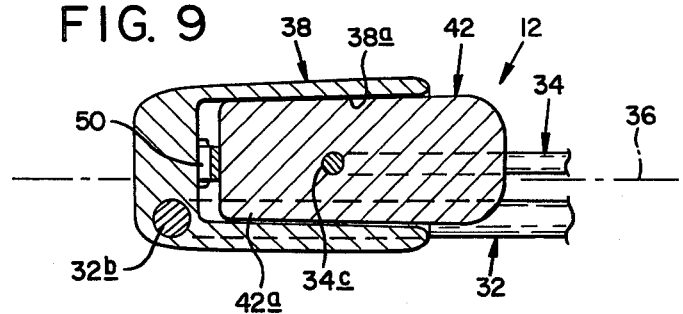

POSITIVE RELEASE FACE-BOW/MOUTH-BOW MECHANISM

BACKGROUND AND SUMMARY OF THE INVENTION

This invention pertains to an improved-safety orthodontic mouth-bow/face-bow mechanism, and more particularly to such a mechanism wherein the mouth-bow and face-bow portions are separable with spring pressure which is developed in the mechanism continually urging these two portions apart when the latter are operatively interengaged.

Dental malocclusions are frequently treated by applying tractive force to the affected teeth by means of "braces". This type of installation generally involves the application of molar bands and an associated buccal tube to the patient's rear teeth, with or without the addition of an arch wire to provide proper tooth alignment.

Tractive force is transmitted to the molars by means of a mouth-bow/face-bow mechanism, which is attached to an elastic head or neck band. Typically, though not in all instances, the mouth-bow/face-bow mechanism employed is a unitary structure where the mouth-bow and face-bow portions are inseparable.

Generally, patients who are treated for dental malocclusions are preteen or teenage individuals. Some are required to wear a face-bow/mouth-bow mechanism, and an associated elastic head or neck band, on a time-extensive basis. As a consequence, such patients frequently come in contact with their peers, who have on occasion in the past, either intentionally or accidentally, pulled a face-bow away from patients' faces and released their grip on the device. This act results in an extremely dangerous condition where the mouth-bow and face-bow portions either cannot separate, or if they are designed to separate, become stuck together so that they don't separate. Such a condition is one where the sharp ends of the mouth-bow are substantially aligned with a patient's eyes as the mouth bow snaps back toward the patient's face, and there have been numerous reported accidents where patients have lost their eyesight as the result of just such an incident.

Safety mechanisms of various types have been proposed to eliminate the hazard to a patient caused by a mouth-bow striking the face. One such device is a safety head gear assembly, which separates at a point of connection between a face-bow and head band upon being pulled, thereby eliminating the tractive force which brings the mouth-bow back into a patient's face. Another approach has been to make the mouth-bow and face-bow portions separable under tension so that a pull on a face-bow does not transmit a pull on a mouth-bow. However, while such apparatus has been useful, it has not always proven to be foolproof and there is, consequently, a continual interest in providing further safety protection.

A general object of the present invention, accordingly, is to provide a unique safety-release face-bow/-mouth-bow combination, which will transmit the desired range of orthodontic tractive tension and which will positively separate, face-bow from mouth-bow, when such tension is released.

According to a preferred embodiment of the invention the proposed positive release mechanism includes two compression-transmission connectors, one mounted on a face-bow and the other mounted on a mouth-bow, which connectors coact with each other to provide appropriate compression transmission during patient use. One connector carries a spring parting means which acts forceably and positively to separate the two connectors when compression transmission is relaxed. In the preferred embodiment, the spring parting means is carried on the connector associated with the face-bow. It takes the form of an elastomer band which surrounds the face-bow connector perpendicular to what might be thought of as the plane of the face-bow. The face-bow connector has an open-ended socket which freely receives the mouth-bow connector. The band has a stretch extending across the face-bow socket which is forced into the socket when the face-bow and mouth-bow connectors are operatively connected.

In another embodiment of the invention, the spring parting means is also an elastomer band which, in this case, stretches around the face-bow connector, and across such an open-ended socket, generally in the plane of the connector.

Further embodiments are described herein where the spring parting means takes the form of either a coil or leaf spring.

Considering the preferred embodiment of the invention in normal usage, the mouth-bow is inserted into buccal tubes conventionally mounted on a patient's teeth, the mouth-bow and face-bow connectors are connected, and the face-bow is connected to a head-band assembly of the type which provides the required compression transmission. Tension in the head-band assembly is transmitted to the face-bow, through the connectors, to the mouth-bow and ultimately to the teeth undergoing treatment. If pressure on the face-bow is released, the elastomer band positively forces the connectors apart, thereby promoting retention of the mouth-bow in the patient's mouth and eliminating the possibility that the mouth-bow will snap back into either the patient's mouth or face causing injury.

These and other objects and advantages attained by the invention will be come more fully apparent as the description which now follows is read in conjunction with the accompanying drawings.

DESCRIPTION OF THE DRAWINGS

FIG. 1 is a simplified, fragmentary perspective view showing a patient wearing orthodontic head gear which employs a positive-release face-bow/mouth-bow mechanism constructed in accordance with the present invention.

FIG. 2 is an enlarged, fragmentary top plan view illustrating details of construction and installation of the face-bow/mouth-bow, mechanism of FIG. 1, with certain parts shown in different positions.

FIG. 3 is a median cross-sectional view taken generally along the line 3—3 in FIG. 1.

FIG. 4 is a fragmentary top plan view illustrating a modification of the invention, with certain parts shown in different positions.

FIG. 5 is a median cross-sectional view taken generally along the line 5—5 in FIG. 4, rotated 90° clockwise.

FIG. 6 is a fragmentary top plan view of another modification of the invention with certain parts shown in different positions.

FIG. 7 is a median cross-sectional view taken generally along the line 7—7 in FIG. 6, rotated 90° clockwise.

FIG. 8 is a fragmentary top plan view of a further modification of the embodiment of the device.

FIG. 9 is a medium cross-sectional view taken generally along the line 8—8 in FIG. 7, rotated 90° clockwise.

DETAILED DESCRIPTION OF THE INVENTION

Turning now the drawings, and referring first of all to FIGS. 1-3, inclusive, indicated generally at 10 is a head gear assembly including a positive-release, or positive-separation face-bow/mouth-bow mechanism 12 constructed in accordance with the invention coupled to a commercially available neck-strap assembly 14 shown in use by a patient to apply a retractive force on the patient's lower jaw. The neck-strap assembly is similar to one set forth in U.S. Pat. No. 4,226,589 entitled "Orthodontic Headgear Release Assembly" and will not be described further herein except to point out that it includes a pair of attaching ends 14a which are removably connected, as will be explained later, to portions in mechanism 12.

Focusing attention for a moment on FIG. 2, here there are shown generally at 16 the arch of teeth carried in the patient's lower jaw. Teeth 16 are banded in a conventional manner with an arch wire 18 suitably secured to selected bands to produce the desired intermaxillary forces between the teeth. Molars in the patient's lower jaw, shown at 20, 22 carry bands 24, 26, respectively on the buccal sides of which are anchored conventional buccal tubes 28, 30, respectively. It is through tubes 28, 30 that the face-bow/mouth-bow mechanism of the invention applies retractive corrective force to the patient's lower jaw.

Returning attention now to FIGS. 1, 2 and 3 collectively, accordingly to the invention mechanism 12 includes a curved face-bow 32 and a curved mouth-bow 34. The face-bow and mouth-bow may be thought of as generally planar devices which, as depicted herein, lie, when coacting, in a common plane shown at 36 in FIG. 3, which plane is substantially parallel to the plane of FIG. 2. The face-bow, as viewed in FIG. 2, has the curved and bent configuration shown, with the face-bow having rear end hooks 32a which connect with previously mentioned attaching ends 14a, and central, forward, generally U-shaped projection 32b whose purpose will be explained shortly.

Joined to the face-bow according to the invention, at the location of projection 32b, is what is referred to herein as a face-bow, compression-transmission coupling 38. Coupling 38 is preferably formed of a suitable plastic material, and is joined to projection 32b by an suitable technique, such as by molding onto the projection. As can be seen in FIG. 3, coupling 38 is a generally planar unit lying substantially in plane 36. According to the invention, coupling 38 includes a rearwardly facing open-ended socket 38a. Extending substantially centrally about the coupling in a plane substantially normal to plane 36 is a groove 38b which receives, in the embodiment of the invention now being described, an endless elastomer band, or a spring parting means, 40, whose function will be explained shortly.

Mouth-bow 34 has the curved and bent configuration shown clearly in FIG. 2 including rear-end attaching portions 34a which are defined, so-to-speak, by reverse bend kinks 34b in the mouth-bow. Like face-bow 32, mouth-bow 34 also includes a front generally U-shaped projection 34c.

Joined as by molding to the mouth-bow, at the location of projection 34c, is a mouth-bow, compression-transmission coupling 42 which is also plastic in the embodiment of the invention now being described. Coupling 42 includes a forwardly projecting tongue 42a which is sized to fit freely within previously mentioned socket 38a. Formed on the upper front and lower central portion of tongue 42a is a groove 42b whose purpose will become apparent shortly.

Explaining now how mechanism 12 performs during normal use, mouth-bow 34 is installed as shown in FIG. 2 with end portions 34a received as illustrated within buccal tubes 28, 30. Face-bow 32 is then coupled to the mouth-bow, against the biasing action of band 40, with tongue 42a extending as shown into socket 38a and with a run of the elastomer band, shown at 40a (FIGS. 2 and 3) stretched and seated within groove 42b. In this condition, hooks 32a are attached to ends 14a in neck-strap assembly 14.

The installed and operative condition of the entire head gear assembly is as illustrated in solid lines in FIGS. 1, 2 and 3. In this condition, tension developed in the neck-strap assembly is transmitted through the face-bow, through couplings 42, 38 and through the mouth-bow to the lower jaw. This condition continues so long as there is no disruption of the head gear assembly. In this regard, it should be pointed out that couplings 38, 40 permit a certain amount of relative angulation between the mouth-bow and face-bow within the planes thereof to accommodate wearer comfort.

Should something happen which tends to pull the face-bow away from the separable mouth-bow, elastomer band 40 produces a positive separation between couplings 38, 42 in a manner assuring that the mouth-bow cannot be withdrawn as a consequence of face-bow movement. This situation is illustrated in FIG. 2 with the face-bow drawn away from the mouth-bow and shown in dashed lines in the figure.

Because of this positive-separation action, the likelihood of a facial injury of the type mentioned earlier is substantially completely avoided. Positive separation produced by the elastomer band assures that slight frictional binding which might tend to occur between couplings 38, 40 cannot defeat the intended separation between the mouth-bow and face-bow.

When such a separation occurs, and it is desired to restore the overall head gear assembly to an operative condition, the face-bow is simply returned to the condition in which it is shown in solid lines in FIGS. 1, 2, 3 relative to the mouth-bow.

FIGS. 4 and 5, 6 and 7, and 8 and 9, respectively, show three different modifications of the invention wherein the modifications relate primarily to the construction and operation of the spring parting means. In all other respects, except as will be pointed out particularly below, and except with respect to the specific shapes of parts, the mechanisms shown in these modifications are substantially the same as the one which has just been described. Accordingly, and in order to avoid number prolixity, reference numbers which are the same as those used in connection with FIGS. 1, 2 and 3 are used to denote structures which are functionally the same as corresponding structures in mechanism 12.

Addressing attention then, first to FIGS. 4 and 5, here, elastomer band 40 extends in a groove 38b which generally circumscribes face-bow coupling 38 in the plane of the coupling. Thus, a stretch 40a in the band is disposed to extend across the open end of socket 38a under a circumstance with couplings 38, 42 separated. In order to accommodate this changed disposition band 40, the front and sides of tongue 42a in coupling 42 include groove 42b, which catches band stretch 40a when the couplings are fitted with one another as shown in solid lines in FIGS. 4 and 5. Thus, the principal difference between the embodiment shown in these two figures and that shown and described with reference to FIGS. 1, 2 and 3 is that the elastomer band which functions as the spring parting means operates in what might be thought of as the planes of the couplings, rather than in a plane which is normal thereto.

Positive separation between the mouth-bow and face-bow occurs with the same effectiveness described earlier in conjunction with FIGS. 1, 2 and 3. In dashed lines in FIG. 4, such a separation is depicted.

Addressing now FIGS. 6 and 7, here the spring parting means takes the form of a coil spring 44 which seats in a well 46 formed in the base of socket 38a. When spring 44 is completely relaxed as is shown in dashed lines in FIG. 6, it extends as shown a substantial distance into socket 38b. The end of the spring which extends into the socket engages a depression 48 which is formed in the outer end of tongue 42b in mouth-bow coupling 42.

In solid lines in FIGS. 6 and 7, couplings 38, 40 are shown in the conditions which they occupy during normal head gear assembly usage. Any action which tends to pull the face-bow away from a user's face results in spring 44 reacting to produce a positive separation between the mouth-bow and face-bow. A separated condition of the face-bow, vis-a-vis the mouth-bow is shown in dashed lines in FIG. 6. In FIGS. 8 and 9, the spring parting means in mechanism 12 takes the form of a bent leaf spring 50 which fits as shown adjacent the base of socket 38a. With couplings 38, 42 interacting as shown in solid lines in these two figures, the outer forward end of tongue 42b presses against the central bulging portion in spring 50, flattening the spring as is shown in solid lines in the figures. Under conditions like those described above relating to pulling of the face-bow away from a user's face, spring 50 relaxes with a bulge extending into socket 38a effecting positive separation between the mouth-bow and face-bow. In FIG. 8, the face-bow is shown in dashed lines in a condition separated from the mouth-bow.

Thus it should be apparent how a face-bow/mouth-bow mechanism may be constructed in accordance with the invention to assure positive spring-biased separation between a separable mouth-bow and face-bow under circumstances with the face-bow drawn away from a user's face. While a preferred embodiment of the invention, and several modifications thereof, have been shown and described, it is appreciated that other variations and modifications may be made without departing from the spirit of the invention. For example, the functions of the mouth-bow and face-bow couplings, vis-a-vis their specific associations with the mouth-bow and face-bow, respectively, may be reversed in the sense that the mouth-bow coupling could be one formed with a socket, and the face-bow coupling one formed with a tongue for receipt in such a socket.

It is claimed and desired to secure by letters patent:

1. A safety release mechanism in the orthodontic combination of a curved mouth-bow device and a curved face-bow device which are separable from one another, where, during use, the face-bow device is designed to impart compressive force to the mouth-bow device, said mechanism comprising
    a pair of compression-transmission couplings one for each of such two devices, operatively interactable with one another to transmit a compressive force between the two devices, and
    spring parting means operatively associated with said two couplings, functioning, with the couplings interacting to transmit such a compressive force between the devices, to urge the devices freely apart from one another.

2. The mechanism of claim 1, wherein said spring parting means comprises elastomer means which tenses with the two couplings interacting as described.

3. The mechanism of claim 2, wherein said elastomer means takes the form of an elongated endless loop carried by one of the two couplings.

4. The mechanism of claim 3, wherein said one coupling is generally planar with an open-ended socket disposed substantially in such plane, the other coupling includes a generally planar tongue freely fitable within said socket, and said loop is disposed in a plane which is substantially normal to the first-mentioned plane, with a stretch of the loop extending deformably across the open end of the socket.

5. The mechanism of claim 4, wherein said other coupling includes a groove for receiving said stretch with the two couplings interacting as described.

6. The mechanism of claim 3, wherein said one coupling is generally planar with an open-ended socket disposed substantially in such plane, the other coupling includes a generally planar tongue freely fitable within said socket, and said loop is disposed substantially in such plane, with a stretch of the loop extending deformably across the open end of socket.

7. The mechanism of claim 6, wherein said other coupling includes a groove for receiving said stretch with the two couplings interacting as described.

8. The mechanism of claim 3, wherein said one coupling is joined to the face-bow device.

9. The mechanism of claim 8, wherein said one coupling is generally planar with an open-ended socket disposed substantially in such plane, the other coupling includes a generally planar tongue freely fitable within said socket, and said loop is disposed in a plane which is substantially normal to the first-mentioned plane, with a stretch of the loop extending deformably across the open end of the socket.

10. The mechanism of claim 9, wherein said other coupling includes a groove for receiving said stretch with the two couplings interacting as described.

11. The mechanism of claim 8, wherein said one coupling is generally planar with an open-ended socket disposed substantially in such plane, the other coupling includes a generally planar tongue freely fitable within said socket, and said loop is disposed substantially in the first-mentioned plane, with a stretch of the loop extending deformably across the open end of socket.

12. The mechanism of claim 11, wherein said other coupling includes a groove for receiving said stretch with the two couplings interacting as described.

13. The mechanism of claim 1, wherein said spring parting means comprises a deformable coil spring.

14. The mechanism of claim 13, wherein one of said couplings is generally planar with an open-ended socket disposed substantially in such plane, the other coupling includes a generally planar tongue freely fitable within said socket, and said spring is mounted on said one coupling, and when in a nondeformed condition extends into said socket.

15. The mechanism of claim 14, wherein said one coupling is attached to the face-bow device.

16. The mechanism of claim 1, wherein said spring parting means comprises a leaf-like spring.

17. The mechanism of claim 16, wherein one of said couplings is generally planar with an open-ended socket disposed substantially in such plane, the other coupling includes a generally planar tongue freely fitable within said socket, and said spring is mounted on said one coupling, and when in a nondeformed condition extends into said socket.

18. The mechanism of claim 17, wherein said one coupling is attached to the face-bow device.

* * * * *